United States Patent
Yamamoto et al.

(10) Patent No.: US 7,638,575 B2
(45) Date of Patent: Dec. 29, 2009

(54) SURFACE TREATING AGENT, FLUORINE-CONTAINING MONOMER AND FLUORINE-CONTAINING POLYMER

(75) Inventors: Ikuo Yamamoto, Osaka (JP); Yutaka Ohira, Osaka (JP); Yoshio Funakoshi, Osaka (JP); Shinichi Minami, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 114 days.

(21) Appl. No.: 10/594,011

(22) PCT Filed: Mar. 25, 2005

(86) PCT No.: PCT/JP2005/005495

§ 371 (c)(1),
(2), (4) Date: Sep. 25, 2006

(87) PCT Pub. No.: WO2005/092997

PCT Pub. Date: Oct. 6, 2005

(65) Prior Publication Data

US 2007/0173148 A1    Jul. 26, 2007

(30) Foreign Application Priority Data

Mar. 26, 2004 (JP) .................... 2004-090929

(51) Int. Cl.
*C08L 27/12* (2006.01)
(52) U.S. Cl. .................. 524/544; 524/556; 524/560; 524/805; 526/243; 526/245; 526/248
(58) Field of Classification Search ............. 524/544; 526/245
See application file for complete search history.

(56) References Cited

U.S. PATENT DOCUMENTS

| | | | |
|---|---|---|---|
| 2,521,902 A | 9/1950 | Coover, Jr. et al. | |
| 3,655,732 A | 4/1972 | Rondestvedt, Jr. | |
| 3,655,752 A | 4/1972 | Roundestvedt, Jr. | |
| 3,773,826 A | 11/1973 | Roundestvedt, Jr. | |
| 3,916,053 A | 10/1975 | Sherman et al. | |
| 4,366,299 A | 12/1982 | Dessaint | |
| 5,055,538 A | 10/1991 | Amimoto et al. | |
| 5,069,941 A * | 12/1991 | Ohmori et al. ............ | 427/385.5 |
| 5,239,026 A * | 8/1993 | Babirad et al. ............ | 526/245 |
| 5,439,998 A | 8/1995 | Lina et al. | |
| 2006/0269741 A1* | 11/2006 | Izumi et al. ............ | 428/336 |

FOREIGN PATENT DOCUMENTS

| | | |
|---|---|---|
| DE | 100 50 391 A1 | 4/2002 |
| EP | 0 190 993 A1 | 8/1986 |
| EP | 0 195 714 A1 | 9/1986 |
| EP | 0 247 489 A2 | 12/1987 |
| EP | 0 294 648 A2 | 12/1988 |
| EP | 0 333 083 A2 | 9/1989 |
| EP | 0 337 474 A2 | 10/1989 |
| EP | 0 426 530 A1 | 5/1991 |
| JP | 63-90588 A | 4/1988 |
| JP | 63-99285 A | 4/1988 |
| JP | 64-56711 A | 3/1989 |
| JP | 1-315471 A | 12/1989 |
| JP | 2-28270 A | 1/1990 |
| JP | 03-103409 | 4/1991 |
| JP | 2000-298345 | 10/2000 |
| JP | 2003-154307 | 5/2003 |
| WO | WO 03/022906 A1 | 3/2003 |
| WO | WO2004078476 A1 * | 9/2004 |

OTHER PUBLICATIONS

Shinobu et al. Chem. Abstract 2004:754491 "Layered Product, Optical Part, Processes for Producing These, and Coating Fluid", 2004, 2 pages.*
Takashige Maedawa, "Fluorine-Containing Surface Modifying Agents", Fine Chemical, vol. 23, No. 6, 1994, pp. 12-25.
US. Environmental Protection Agency, Office of Pollution Prevention and Toxics., Risk Assessment Division, Preliminary Risk Assessment of the Developmental Toxicity Associated With Exposure to Perfluorooctanoic Acid and Its Salts, Apr. 10, 2003, pp. 1-61, http://www.epa.gov/opptintr/pfoa/pfoara.pdf.
US. Environmental Protection Agency, "Perfluorooctanoic Acid (PFOA), Fluorinated Telomers; Request for Comment, Solicitaion of Interested Parties for Enfoceable Consent Agreement Development, and Notice of Public Meeting", Federal Register, vol. 68, No. 73, Wednesday, Apr. 16, 2003 / Notices, pp. 18626-18633, [FRL-7303-8]., http://www.epa.gov/opptintr/pfoa/pfoafr.pdf.
US. Environmental Protection Agency, "EPA Intensifies Scientific Investigation of a Chemical Processing Aid", EPA Environmental News, Monday Apr. 14, 2003., 3 pages, http://www.epa.gov/opptintr/pfoa/pfoaprs.pdf.
US. Environmental Protection Agency, EPA OPPT Fact Sheet, Apr. 14, 2003., hppt://www.epa.gov/opptintr/pfoa/pfoafacts.pdf.

* cited by examiner

*Primary Examiner*—Marc S Zimmer
*Assistant Examiner*—Nicole M Buie
(74) *Attorney, Agent, or Firm*—Sughrue Mion, PLLC

(57) ABSTRACT

Disclosed is a surface treating agent containing fluorine-containing polymer having:
(A) a repeating unit derived from a fluorine-containing compound which is represented by the following formula:

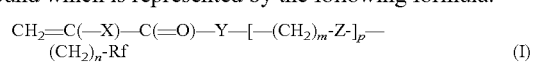

$$CH_2=C(-X)-C(=O)-Y-[-(CH_2)_m-Z-]_p-(CH_2)_n-Rf \quad (I)$$

(wherein X is a hydrogen atom or a methyl group),
(B) a repeating unit derived from a monomer containing no fluorine atom, if necessary and (C) a repeating unit derived from a crosslinkable monomer, if necessary. This surface treating agent has excellent water repellency, oil repellency and antifouling property.

20 Claims, No Drawings

SURFACE TREATING AGENT, FLUORINE-CONTAINING MONOMER AND FLUORINE-CONTAINING POLYMER

TECHNICAL FIELD

The present invention relates to a polymer and a treatment which impart excellent water repellency, oil repellency and soil resistance to a textile, a masonry, a filter (for example, an electrostatic filter), a dust protective mask, and a part of fuel cell.

BACKGROUND ART

Hitherto, various fluorine-containing compounds are proposed. The fluorine-containing compounds have the advantageous effects of having properties excellent in heat resistance, oxidation resistance, weather resistance and the like. The fluorine-containing compounds are used as, for example, the water- and oil-repellent agent and soil release agent by utilizing the properties that the fluorine-containing compounds have low free energy, i.e., difficulty in adherence.

Examples of the fluorine-containing compounds used as the water- and oil-repellent agent include a fluorine-containing polymer having repeating units derived from (meth)acrylate ester having a fluoroalkyl group. It is proposed that a (meth)acrylate ester having a spacer which is an organic group positioned between an acrylate group and a fluoroalkyl group is used in the fluorine-containing polymer. Such fluorine-containing polymers having the spacer are disclosed in, for example, U.S. Pat. No. 3,655,732, U.S. Pat. No. 3,773, 826, U.S. Pat. No. 3,916,053 and U.S. Pat. No. 5,439,998. These fluorine-containing polymers, however, could not impart sufficient water- and oil-repellency.

Various recent research results indicate that in view of the practical treatment of fibers with the surface treatment agent (particularly the water- and oil-repellent agent), the important surface property is not a static contact angle, but is a dynamic contact angle, particularly a reversing contact angle. That is, the advancing contact angle of water is not dependent on the carbon number of the fluoroalkyl side chain, but the reversing contact angle of water in the case of carbon number of at most 7 is remarkably low than that in the case of carbon number of at least 8. In correspondence to this, an X ray analysis shows that the side chain crystallizes when the carbon number of side chain is at least 7. It is known that the actual water repellency has correlation with the crystallization of the side chain and that mobility of the surface treatment agent molecules is an important factor for expression of the actual performances (for example, MAEKAWA takashige, FINE CHEMICAL, Vol. 23, No. 6, page 12 (1994)). Accordingly, it is believed that the acrylate polymer having low carbon number of fluoroalkyl group in the side chain which is at most 7 (particularly at most 6) has low crystallinity so that the polymer cannot satisfy the actual performances (particularly water repellency).

JP-A-63-90588, JP-A-63-99285 and JP-A-01-315471 disclose that a fluorine-containing acrylate polymer wherein the alpha-position is substituted with fluorine, chlorine or the like has excellent properties such as good adhesion to a substrate, high strength of a film and good water- and oil-repellency. These publications describe that the fluoroalkyl group used in Examples has at least 8 carbon atoms and does not suggest to use the acrylate monomer having the fluoroalkyl group having at most 6 carbon atoms.

Recent study results (EPA Report "PRELIMINARY RISK ASSESSMENT OF THE DEVELOPMENTAL TOXICITY ASSOCIATED WITH EXPOSURE TO PERFLUOROOCTANOIC ACID AND ITS SALTS" and the like clarify that a PFOA (perfluorooctanoic acid) doubtfully has a potential risk of environmental load. EPA (Environmental Protection Agency of USA) announced on Apr. 14, 2003 that the EPA intensifies the scientific investigation on PFOA.

On the other hand, Federal Register (FR Vol. 68, No. 73/Apr. 16, 2003 [FRL-2303-8]) EPA Environmental News for release Monday Apr. 2003 "EPA INTENSIFIES SCIENTIFIC INVESTIGATION OF A CHEMICAL PROCESSING AID", and EPA OPPT FACT SHEET Apr. 14, 2003 announced that a "telomer"may possibly metabolize or decompose to PFOA. It is also announced that the "telomer"is used in a large number of commercial products including fire fighting foams, care products and cleaning products as well as soil, stain and grease resistant coating on carpets, textiles, paper, and leather.

DISCLOSURE OF THE INVENTION

Problems to be Solved by the Invention

An object of the present invention is to provide a surface treatment agent having excellent water- and oil-repellency and soil resistance even if the fluoroalkyl group in the fluorine-containing polymer has the carbon number of at most 6.

Means for Solving the Problems

The present invention provides a surface treatment agent comprising (1) a fluorine-containing polymer and (2) water and/or an organic solvent, characterized in that the fluorine-containing polymer comprises repeating units derived from a fluorine-containing compound of the formula:

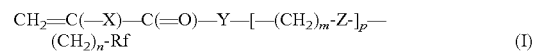

$$CH_2=C(-X)-C(=O)-Y-[-(CH_2)_m-Z-]_p-(CH_2)_n-Rf \qquad (I)$$

wherein X is a hydrogen atom or a methyl group;
Y is —O— or —NH—;
Z is —S— or —SO$_2$—;
Rf is a fluoroalkyl group having 1 to 6 carbon atoms;
m is from 1 to 10, n is from 0 to 10, and p is 0 or 1.

The present invention provides (a) a fluorine-containing compound of the formula:

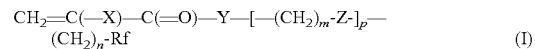

$$CH_2=C(-X)-C(=O)-Y-[-(CH_2)_m-Z-]_p-(CH_2)_n-Rf \qquad (I)$$

wherein X is a hydrogen atom or a methyl group;
Y is —O— or —NH—;
Z is —S—;
Rf is a fluoroalkyl group having 1 to 6 carbon atoms;
m is from 1 to 10, n is from 0 to 10, and p is 0 or 1;
provided that when p is 0, Y is —NH— and that when p is 1, Y is —O— and n is 0.

The present invention provides a fluorine-containing polymer comprising (A) repeating units derived from the above-mentioned fluorine-containing compound (a) (that is, a fluorine-containing compound (a)).

EFFECTS OF THE INVENTION

The present invention can give a surface treatment agent excellent in water repellency, oil repellency and antifouling property.

BEST MODE OF CARRYING OUT THE INVENTION

The fluorine-containing polymer of the present invention comprises (A) repeating units derived from (a) the fluorine-containing compound of the formula:

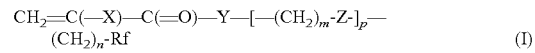

$$CH_2=C(-X)-C(=O)-Y-[-(CH_2)_m-Z-]_p-(CH_2)_n-Rf \qquad (I)$$

wherein X is a hydrogen atom or a methyl group;
Y is —O— or —NH—;
Z is —S— or —SO$_2$—;
Rf is a fluoroalkyl group having 1 to 6 carbon atoms;
m is from 1 to 10, n is from 0 to 10, and p is 0 or 1.

That is, the fluorine-containing polymer forming the surface treatment agent comprises (A) repeating units derived from the above-mentioned fluorine-containing compound (a).

The fluorine-containing polymer is a homopolymer or copolymer.

In the case that the fluorine-containing polymer is the copolymer, the fluorine-containing polymer may contain:
(B) repeating units derived from a monomer free from a fluorine atom, and
(C) optionally, repeating units derived from a crosslinkable monomer,
in addition to the repeating unit (A).

In the present invention, the repeating unit (A) is formed by the fluorine-containing compound (a) of the formula (I).

In the above-mentioned formula, the Rf group is preferably a perfluoroalkyl group. The carbon number of the Rf group is from 1 to 6, for example, from 1 to 4. Examples of the Rf group are —CF$_3$, —CF$_2$CF$_3$, —CF$_2$CF$_2$CF$_3$, —CF(CF$_3$)$_2$, —CF$_2$CF$_2$CF$_2$CF$_3$, —CF$_2$CF(CF$_3$)$_2$, —C(CF$_3$)$_3$, —(CF$_2$)$_4$CF$_3$, —(CF$_2$)$_2$CF(CF$_3$)$_2$, —CF$_2$C(CF$_3$)$_3$, —CF(CF$_3$)CF$_2$CF$_2$CF$_3$, —(CF$_2$)$_5$CF$_3$ and —(CF$_2$)$_3$CF(CF$_3$)$_2$.

m may be, for example, from 2 to 10, and n may be, for example, from 1 to 10.

Preferably, p is 1 when Y is —O—, and p is 0 when Y is —NH—.

Examples of the fluorine-containing compound (a) are the followings.
CH$_2$=C(—X)—C(=O)—O—(CH$_2$)$_m$—S—(CH$_2$)$_n$-Rf
CH$_2$=C(—X)—C(=O)—O—(CH$_2$)$_m$—SO$_2$—(CH$_2$)$_n$-Rf
CH$_2$=C(—X)—C(=O)—NH—(CH$_2$)$_n$-Rf
wherein X is a hydrogen atom or a methyl group;
Rf is a fluoroalkyl group having 1 to 6;
m is from 1 to 10, and n is from 0 to 10.

Specific examples of the fluorine-containing compound (a) are followings:
CH$_2$=CH—C(=O)—O—(CH$_2$)$_2$—S-Rf
CH$_2$=CH—C(=O)—O—(CH$_2$)$_2$—S—(CH$_2$)$_2$-Rf
CH$_2$=CH—C(=O)—O—(CH$_2$)$_2$—SO$_2$-Rf
CH$_2$=CH—C(=O)—O—(CH$_2$)$_2$—SO$_2$—(CH$_2$)$_2$-Rf
CH$_2$=CH—C(=O)—NH—(CH$_2$)$_2$-Rf
CH$_2$=C(—CH$_3$)—C(=O)—O—(CH$_2$)$_2$—S-Rf
CH$_2$=C(—CH$_3$)—C(=O)—O—(CH$_2$)$_2$—S—(CH$_2$)$_2$-Rf
CH$_2$=C(—CH$_3$)—C(=O)—O—(CH$_2$)$_2$—SO$_2$-Rf
CH$_2$=C(—CH$_3$)—C(=O)—O—(CH$_2$)$_2$—SO$_2$—(CH$_2$)$_2$-Rf
CH$_2$=C(—CH$_3$)—C(=O)—NH—(CH$_2$)$_2$-Rf
CH$_2$=CH—C(=O)—O—(CH$_2$)$_3$—S-Rf
CH$_2$=CH—C(=O)—O—(CH$_2$)$_3$—S—(CH$_2$)$_2$-Rf
CH$_2$=CH—C(=O)—O—(CH$_2$)$_3$—SO$_2$-Rf
CH$_2$=CH—C(=O)—O—(CH$_2$)$_3$—SO$_2$—(CH$_2$)$_2$-Rf
CH$_2$=C(—CH$_3$)—C(=O)—O—(CH$_2$)$_3$—S-Rf
CH$_2$=C(—CH$_3$)—C(=O)—O—(CH$_2$)$_3$—S—(CH$_2$)$_2$-Rf
CH$_2$=C(—CH$_3$)—C(=O)—O—(CH$_2$)$_3$—SO$_2$-Rf
CH$_2$=C(—CH$_3$)—C(=O)—O—(CH$_2$)$_3$—SO$_2$—(CH$_2$)$_2$-Rf
wherein Rf is a fluoroalkyl group having 1 to 6.

The following fluorine-containing compounds are novel compounds.

$$CH_2=C(-X)-C(=O)-O-(CH_2)_m-S-Rf \quad (1)$$

$$CH_2=C(-X)-C(=O)-NH-(CH_2)_n-Rf \quad (2)$$

wherein m is from 1 to 10, and n is from 0 to 10.

The fluorine-containing compounds (1) and (2) can be prepared, for example, as follows.

Fluorine-containing Compound (1)

Mercaptoethanol is reacted with perfluoroalkyl iodide having a Rf group having one end substituted with iodine in a solvent (for example, water/DMF), for example, at 30° C. to 90° C. for 0.5 hours to 30 hours to give a perfluoroalkyl thioethanol. This alcohol is reacted with acrylic acid in a solvent (for example, cyclohexane) in the presence of a catalyst (for example, paratoluene sulfonic acid), for example, at 30° C. to 70° C. for 0.5 hours to 30 hours to give perfluoroalkylthioethyl acrylate.

Fluorine-containing Compound (2)

Into a reactor, tridecylmethyl ammonium chloride, perfluoroalkylethyl iodide having Rf group substituted with iodine at one end, and an aqueous solution of sodium azide are added (for example, at room temperature), and reacted with stirring and heating (for example, at 50 to 95° C., particularly at 90° C.) for 1 to 50 hours (for example, 20 hours). After the completion of the reaction, the disappearance of the raw material, that is, the iodine compound is confirmed by GC (gas chromatography). The reaction liquid is cooled to room temperature (23° C.), and a lower organic layer is separated. An aqueous layer is extracted with diisopropyl ether, and the extract as such is used in the next reaction.

Into the autoclave, said reaction extract and a catalyst (for example, 10% palladium/carbon) are charged and then a hydrogen gas (for example, at the pressure of 2 to 15 Kg/cm$^2$, particularly 8 Kg/cm$^2$) is added therein. The mixture is stirred, for example, at 10 to 30° C. (particularly room temperature (23° C.)) for 1 to 30 hours (for example, 15 hours). The disappearance of the raw material is confirmed by GC, an organic layer is filtered by celite, and a filtrate as such is used in the following reaction.

Into a flask, triethylamine and 4-t-butyl catechol are added to said solution of amino product in diisopropyl ether under cooling with ice. Then acrylic acid chloride is dropwise added under cooling with ice, and the mixture is stirred at room temperature (23° C.) for 0.5 to 50 hours (for example, 12.5 hours). A produced solid is filtered off, a filtrate is washed with a 5% aqueous solution of citric acid, and an organic layer is dried over magnesium sulfate. The mixture is filtered and a filtrate is concentrated under reduced pressure. A residue is subjected to a silica gel chromatography to give perfluoroalkylethylacrylic acid amide.

The repeating units (B) are derived from (b) the monomer free from a fluorine atom. The monomer (b) is preferably a fluorine-free monomer having a carbon-carbon double bond. The monomer (b) is preferably a vinyl monomer which is free from fluorine. The fluorine atom-free monomer (b) is generally a compound having one carbon-carbon double bond. Preferable examples of the fluorine atom-free monomer (b) include, for example, ethylene, vinyl acetate, vinyl halide (for example, vinyl chloride) vinylidene halide (for example, vinylidene chloride), acrylonitrile, styrene, polyethyleneglycol (meth)acrylate, polypropyleneglycol (meth)acrylate, methoxypolyethylene-glycol (meth)acrylate, methoxypolypropyleneglycol (meth)acrylate, vinyl alkyl ether and isoprene. The fluorine atom-free monomer (b) is not limited to these examples.

The fluorine atom-free monomer (b) may be a (meth)acrylate ester having an alkyl group. The number of carbon atoms of the alkyl group may be from 1 to 30, for example, from 6 to 30, e.g., from 10 to 30. For example, the fluorine atom-free monomer (b) may be acrylates of the general formula:

$$CH_2=CA^1COOA^2$$

wherein $A^1$ is a hydrogen atom or a methyl group, and $A^2$ is an alkyl group represented by $C_nH_{2n+1}$ (n=1 to 30).

The repeating units (C) are derived from the crosslinkable monomer (c). The crosslinkable monomer (c) may be a fluorine-free monomer having at least two reactive groups and/or carbon-carbon double bonds. The crosslinkable monomer (c) may be a compound having at least two carbon-carbon double bonds, or a compound having at least one carbon-carbon double bond and at least one reactive group. Examples of the reactive group include a hydroxyl group, an epoxy group, a chloromethyl group, a blocked isocyanate group, an amino group and a carboxyl group.

Examples of the crosslinkable monomer (c) include diacetoneacrylamide, (meth)acrylamide, N-methylolacrylamide, hydroxymethyl (meth)acrylate, hydroxyethyl (meth)acrylate, 3-chloro-2-hydroxypropyl (meth)acrylate, N,N-dimethylaminoethyl (meth)acrylate, N,N-diethylaminoethyl (meth)acrylate, butadiene, chloroprene and glycidyl (meth)acrylate, to which the crosslinkable monomer is not limited.

The copolymerization with the monomer (b) and/or the monomer (c) can optionally improve various properties such as water- and oil-repellency and soil resistance; cleaning durability and washing durability of said repellency and resistance; solubility in solvent; hardness; and feeling.

In the fluorine-containing polymer, the amount of the fluorine atom-free monomer (b) may be, from 0 to 500 parts by weight, for example, from 0.1 to 100 parts by weight, particularly from 0.1 to 50 parts by weight, and the amount of the crosslinkable monomer (c) may be from 0 to 50 parts by weight, for example, from 0 to 20 parts by weight, particularly, from 0.1 to 15 parts by weight, based on 100 parts by weight of the fluorine-containing monomer (a).

The weight-average molecular weight of the fluorine-containing polymer may be, for example, from 2,000 to 5,000,000, particularly from 3,000 to 5,000,000, especially from 10,000 to 1,000,000. The weight-average molecular weight of the fluorine-containing polymer can be measured by GPC (gel permeation chromatography) (in terms of polystyrene).

The fluorine-containing polymer can be produced as follows.

In a solution polymerization, there can be used a method of dissolving the monomer(s) into an organic solvent in the presence of a polymerization initiator, replacing the atmosphere by nitrogen, and stirring the mixture with heating at the temperature within the range from 30° C. to 120° C. for 1 hour to 10 hours. Examples of the polymerization initiator include azobisisobutyronitrile, benzoyl peroxide, di-tert-butyl peroxide, lauryl peroxide, cumene hydroperoxide, t-butyl peroxypivalate and diisopropyl peroxydicarbonate. The polymerization initiator may be used in the amount within the range from 0.01 to 20 parts by weight, for example, from 0.01 to 10 parts by weight, based on 100 parts by weight of the monomers.

The organic solvent is inert to the monomer(s) and dissolves the monomer(s), and examples thereof include acetone, chloroform, HCHC225, isopropyl alcohol, pentane, hexane, heptane, octane, cyclohexane, benzene, toluene, xylene, petroleum ether, tetrahydrofuran, 1,4-dioxane, methyl ethyl ketone, methyl isobutyl ketone, ethyl acetate, butyl acetate, 1,1,2,2-tetrachloroethane, 1,1,1-trichloroethane, trichloroethylene, perchloroethylene, tetrachlorodifluoroethane and trichlorotrifluoroethane. The organic solvent may be used in the amount within the range from 50 to 2,000 parts by weight, for example, from 50 to 1,000 parts by weight, based on 100 parts by weight of total of the monomers.

In an emulsion polymerization, there can be used a method of emulsifying monomers in water in the presence of a polymerization initiator and an emulsifying agent, replacing the atmosphere by nitrogen, and polymerizing with stirring, for example, at the temperature within the range from 50° C. to 80° C. for 1 hour to 10 hours. As the polymerization initiator, for example, water-soluble initiators (e.g., benzoyl peroxide, lauroyl peroxide, t-butyl perbenzoate, 1-hydroxycyclohexyl hydroperoxide, 3-carboxypropionyl peroxide, acetyl peroxide, azobisisobutyl-amidine dihydrochloride, azobisisobutyronitrile, sodium peroxide, potassium persulfate and ammonium persulfate) and oil-soluble initiators (e.g., azobisisobutyronitrile, benzoyl peroxide, di-tert-butyl peroxide, lauryl peroxide, cumene hydroperoxide, t-butyl peroxypivalate and diisopropyl peroxydicarbonate) are used. The polymerization initiator may be used in the amount within the range from 0.01 to 10 parts by weight based on 100 parts by weight of the monomers.

In order to obtain a polymer dispersion in water, which is superior in storage stability, it is desirable that the monomers are atomized in water by using an emulsifying device capable of applying a strong shattering energy (e.g., a high-pressure homogenizer and an ultrasonic homogenizer) and then polymerized with using the oil-soluble polymerization initiator. As the emulsifying agent, various emulsifying agents such as an anionic emulsifying agent, a cationic emulsifying agent and a nonionic emulsifying agent can be used in the amount within the range from 0.5 to 20 parts by weight based on 100 parts by weight of the monomers. An anionic and/or cationic and/or nonionic emulsifying agent is preferably used. When the monomers are not completely compatibilized, a compatibilizing agent (e.g., a water-soluble organic solvent and a low-molecular weight monomer) capable of sufficiently compatibilizing them is preferably added to these monomers. By the addition of the compatibilizing agent, the emulsifiability and polymerizability can be improved.

Examples of the water-soluble organic solvent include acetone, methyl ethyl ketone, ethyl acetate, propylene glycol, dipropylene glycol monomethyl ether, dipropylene glycol, tripropylene glycol and ethanol. The water-soluble organic solvent may be used in the amount within the range from 1 to 50 parts by weight, e.g., from 10 to 40 parts by weight, based on 100 parts by weight of water. Examples of the low-molecular weight monomer include methyl methacrylate, glycidyl methacrylate and 2,2,2-trifluoroethyl methacrylate. The low-molecular weight monomer may be used in the amount within the range from 1 to 50 parts by weight, e.g., from 10 to 40 parts by weight, based on 100 parts by weight of total of monomers.

The surface treatment agent of the present invention is preferably in the form of a solution, an emulsion or an aerosol. The surface treatment agent comprises the fluorine-containing polymer and a medium (particularly an organic solvent and/or water, for example, a liquid medium). The concentration of the fluorine-containing polymer in the surface treatment agent may be, for example, from 0.1 to 50% by weight.

The surface treatment agent can be applied to a substrate to be treated by a know procedure. Usually, the surface treatment agent is diluted or dispersed with an organic solvent or water, is adhered to surfaces of the substrate by a well-known procedure such as an immersion coating, a spray coating and a foam coating, and is dried. If necessary, the surface treatment agent is applied together with a suitable crosslinking agent, followed by curing. It is also possible to add other surface treatment agents (for example, a water repellent agent and an oil repellent agent), or mothproofing agents, softeners, antimicrobial agents, flame retardants, antistatic agents, paint fixing agents, crease-proofing agents, etc. to the surface treatment agent of the present invention. For the immersion coating, the concentration of the fluorine-containing polymer in the treatment liquid contacted with the substrate may be from 0.05 to 10% by weight, based on the treatment liquid. For the spray coating, the concentration of the fluorine-containing polymer in the treatment liquid may be from 0.1 to 5% by weight, based on the treatment liquid. A stain blocker may be used. When the stain blocker is used, it is preferable to use an anionic emulsifier or a nonionic surfactant.

The substrate to be treated with the surface treatment agent (for example, a water- and oil-repellent agent) of the present invention include a textile, masonry, a filter (for example, an electrostatic filter), a dust protective mask, a part of fuel cell (for example, a gaseous diffusion electrode and a gaseous diffusion support), glass, paper, wood, leather, fur, asbestos, brick, cement, metal and oxide, ceramics, plastics, a coated surface and a plaster. The textile may be particularly a carpet. The textile has various examples. Examples of the textile include animal- or vegetable-origin natural fibers such as cotton, hemp, wool and silk; synthetic fibers such as polyamide, polyester, polyvinyl alcohol, polyacrylonitrile, polyvinyl chloride and polypropylene; semi-synthetic fibers such as rayon and acetate; inorganic fibers such as glass fiber, carbon fiber and asbestos fiber; and a mixture of these fibers. The treatment agent of the present invention can be suitably used for carpet made from nylon and/or polypropylene.

The textile may be in any form such as a fiber, a yarn, a fabric and the like. When the carpet is treated with the surface treatment agent of the present invention, the carpet may be formed after treating fibers or yarns with the surface treatment agent, or the formed carpet may be treated with the surface treatment agent.

The "treatment" means that a treatment agent is applied to a substrate by immersion, spraying, coating or the like. The treatment gives the result that the fluorine-containing polymer which is an active component of the treatment agent is penetrated into the internal parts of the substrate and/or adhered to surfaces of the substrate.

EXAMPLES

The following Examples are specifically illustrated but are not to be construed to limit the scope of the invention.

Shower Water Repellency Test

The shower water repellency was expressed by water repellency No. (as shown in the below-described Table 1) conducted according to JIS-L-1092.

TABLE 1

| Water repellency No. | State |
| --- | --- |
| 5 | No wet or adhesion on surface |
| 4 | Slight wet or adhesion on surface |
| 3 | Partial wet on surface |
| 2 | Wet on surface |
| 1 | Complete wet on surface |

Water-repellency Test

A treated fabric is stored in a thermo-hygrostat having a temperature of 21° C. and a humidity of 65% for at least 4 hours. A test liquid (isopropyl alcohol (IPA), water, and a mixture thereof, as shown in Table 2) which has been also stored at 21° C. is used. The test is conducted in an air-conditioned room having a temperature of 21° C. and a humidity of 65%. A droplet of the test liquid in an amount of 0.05 mL is softly dropped by a micropipette on the fabric. If the droplet remains on the fabric after standing for 30 seconds, the test liquid passes the test. The water-repellency is expressed by a point corresponding to a maximum content (% by volume) of isopropyl alcohol (IPA) in the test liquid which passes the test. The water-repellency is evaluated as twelve levels which are Fail, 0, 1, 2, 3, 4, 5, 6, 7, 8, 9 and 10 in order of a poor level to an excellent level.

TABLE 2

| | Water-repellency test liquid | |
| --- | --- | --- |
| | (% by volume) | |
| Point | Isopropyl alcohol | Water |
| 10 | 100 | 0 |
| 9 | 90 | 10 |
| 8 | 80 | 20 |
| 7 | 70 | 30 |
| 6 | 60 | 40 |
| 5 | 50 | 50 |
| 4 | 40 | 60 |
| 3 | 30 | 70 |
| 2 | 20 | 80 |
| 1 | 10 | 90 |
| 0 | 0 | 100 |
| Fail | Inferior to isopropyl alcohol 0/water 100 | |

Oil-repellency Test

A treated fabric is stored in a thermo-hygrostat having a temperature of 21° C. and a humidity of 65% for at least 4 hours. A test liquid (shown in Table 3) which has been also stored at 21° C. is used. The test is conducted in an air-conditioned room having a temperature of 21° C. and a humidity of 65%. A droplet of the test liquid in an amount of 0.05 mL is softly dropped by a micropipette on the fabric. If the droplet remains on the fabric after standing for 30 seconds, the test liquid passes the test. The oil-repellency is expressed by a maximum point of the test liquid which passes the test. The oil-repellency is evaluated as nine levels which are Fail, 1, 2, 3, 4, 5, 6, 7 and 8 in order of a poor level to an excellent level.

TABLE 3

Oil-repellency test liquid

| Point | Test liquid | Surface tension (dyne/cm, 25° C.) |
|---|---|---|
| 8 | n-Heptane | 20.0 |
| 7 | n-Octane | 21.8 |
| 6 | n-Decane | 23.5 |
| 5 | n-Dodecane | 25.0 |
| 4 | n-Tetradecane | 26.7 |
| 3 | n-Hexadecane | 27.3 |
| 2 | Mixture liquid of n-Hexadecane 35/nujol 65 | 29.6 |
| 1 | Nujol | 31.2 |
| Fail | Inferior to 1 | — |

Monomers are synthesized as follows:

Synthetic Example 1 (9FSEA monomer)

Synthesis of 2-(perfluorobutylthio)ethyl acrylate

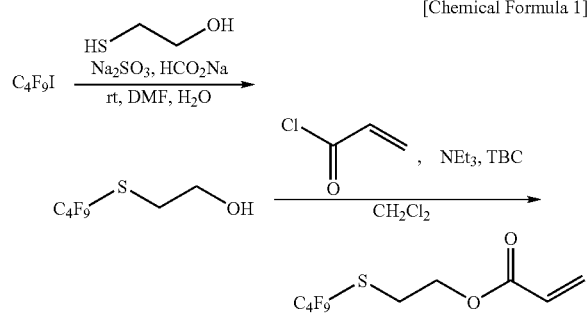

[Chemical Formula 1]

1,1,1,2,2,3,3,4,4-nonafluoro-4-iodobutane (138.4 g (400 mmol)) was dissolved in a mixture liquid of DMF (400 ml) and water (80 ml), and mercaptoethanol (32.2 g (400 mmol)) was added. Further, sodium formate (27.2 g (400 mmol)), sodium sulfite heptahydrate (100.9 g (400 mmol)) were added, and stirred at room temperature (23° C.) for one night. Water (1 L) and isopropyl ether (1 L) were added to the reaction liquid, which was separated. An aqueous layer was further extracted with isopropyl ether (500 ml×2). An organic layer was washed with 10% hydrochloric acid (500 ml), water (500 ml) and a saturated saline solution (500 ml), dried over anhydrous magnesium sulfate and filtered. The solvent was distilled off. A solution of a part (25.9 g, equivalent to 78 mmol) of the condensate [2-(perfluorosulfonyl)ethanol], triethylamine (19.5 g (140 mmol)) and 4-t-butylcatechol (one particle) in dichloromethane (200 ml) was cooled to 0° C. Acryloyl chloride (8.5 ml (10.5 mmol)) was slowly added (The internal temperature increased to 15° C.). After removing the ice bath, the mixture was stirred at room temperature (23° C.) for 1 hour, and the disappearance of the raw material was confirmed by GC. The reaction liquid was washed with a 5% aqueous citric acid, and dried over anhydrous magnesium sulfate. The reaction liquid was filtered and the solvent was distilled off. A fraction of 65 to 67° C./4 mmHg was gathered by the vacuum distillation to give acrylate ester (23.6 g). Yield: 86.4%.

$^1$H NMR(CDCl$_3$; internal standard TMS δppm): 6.46(dd, 1H, J$_{AB}$=1.6 Hz, J$_{AX}$=17.2 Hz, CH$_A$H$_B$=C), 6.14 (dd, 1H, J$_{AX}$=17.2 Hz, J$_{BX}$=10.3 Hz, C=CH$_X$), 5.90 (dd, 1H, J$_{BX}$=10.3 Hz, J$_{AB}$=1.6 Hz, CH$_A$H$_B$=C), 4.40 (t, 2H, J$_{HH}$=6.4 Hz, OCH$_2$), 3.23 (t, 2H, J$_{HH}$=6.4 Hz, CH$_2$S) $^{19}$F NMR(CDCl$_3$; internal standard CFCl$_3$ δppm): −81.5 (m, 3F, CF$_3$), −87.8 (m, 2F, CF$_2$S), −121.2(m, 2F, CF$_2$), −126.0 (m, 2F, CF$_2$).

Synthetic Example 2 (9FESEA monomer)

Synthesis of 2-(3,3,4,4,5,5,6,6,6-nonafluorohexylthio)ethyl acrylate

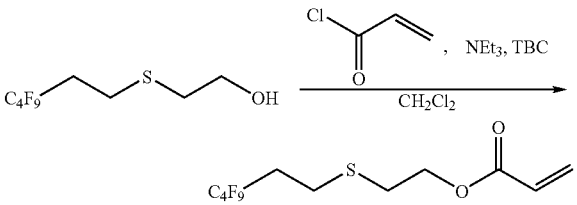

[Chemical Formula 2]

A solution of 2-(3,3,4,4,5,5,6,6,6-nonafluorohexylthio)ethanol (81 g (250 mmol)), triethylamine (52.3 ml (375 mmol)), 4-t-butylcatechol (one particle) and dichloromethane (500 ml) was cooled to 0° C., and acryloyl chloride (24.4 ml (300 mmol)) was slowly added for 10 minutes. The mixture was stirred at room temperature (23° C.) for 40 minutes. The reaction liquid was washed with a 5% aqueous citric acid (500 ml) and a saturated saline solution, and dried over anhydrous magnesium sulfate. The reaction liquid was filtered to give a crude acrylate ester (81.0 g). Yield: 85.7%.

$^1$H NMR(CDCl$_3$; internal standard TMS δppm): 6.45(dd, 1H, J$_{AB}$=1.2 Hz, J$_{AX}$=17.2 Hz, CH$_A$H$_B$=C), 6.14 (dd, 1H, J$_{AX}$=17.2 Hz, J$_{BX}$=10.3 Hz, C=CH$_X$), 5.88 (dd, 1H, J$_{BX}$=10.3 Hz, J$_{AB}$=1.2 Hz, CH$_A$H$_B$=C), 4.36 (t, 2H, J$_{HH}$=6.6 Hz, OCH$_2$), 2.8 (m, 4H, CH$_2$SCH$_2$), 2.4 (m, 2H, CH$_2$CF$_2$) $^{19}$F NMR (CDCl$_3$; internal standard CFCl$_3$ δppm): −81.5(m, 3F, CF$_3$), −115.0 (m, 2F, CF$_2$), −124.8 (m, 2F, CF$_2$), −126.5 (m, 2F, CF$_2$).

Synthetic Example 3 (9FES02EA monomer)

Synthesis of 2-(3,3,4,4,5,5,6,6,6-nonafluorohexylsulfonyl)ethyl acrylate

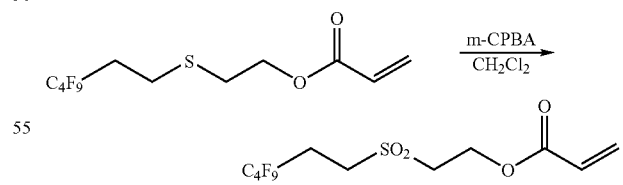

A solution of crude 2-(3,3,4,4,5,5,6,6,6-nonafluoro-hexylthio)ethyl acrylate (81.0 g (214 mmol)) prepared in Synthetic Example 2 and dichloromethane (1.5 L) was cooled with ice and m-chloroperbenzoic acid (100 g (446 mmol)) was gradually added. After the completion of the addition, the mixture was stirred at room temperature (23° C.) for one night, and filtered. The filtrate was washed with a 30% aqueous solution of sodium thiosulfate pentahydrate. After the disappearance of peracid in an aqueous layer was confirmed by a iodine/ starch reaction, an organic layer was washed with a saturated aqueous sodium hydrogen carbonate. The organic layer was dried over magnesium sulfate and filtered. A filtrate was condensed under reduced pressure, and a residue was purified by a silica gel chromatography (n-hexane:ethyl acetate=5:1). A white solid obtained after condensation was dried to give a sulfone substance (55.4 g). Yield: 63.1%.

$^1$H NMR(CDCl$_3$; internal standard TMS δppm): 6.45 (dd, 1H, $J_{AB}$=1.1 HZ, $J_{AX}$=17.3 Hz, CH$_A$H$_B$=C), 6.12 (dd, 1H, $J_{AX}$=17.3 HZ, $J_{BX}$=10.5 Hz, C=CH$_X$), 5.95 (dd, 1H, JB$_X$=10.5 Hz, $J_{AB}$=1.1 HZ, CH$_A$H$_B$=C), 4.65 (t, 2H, $J_{HH}$=5.6 HZ, OCH$_2$), 3.42 (t, 2H, $J_{HH}$=5.7 Hz, CH$_2$SO$_2$), 3.33 (tt, 2H, $J_{HH}$=8.5 Hz, SO$_2$CH$_2$CH$_2$CF$_2$), 2.69 (m, 2H, CH$_2$CF$_2$) $^{19}$F NMR(CDCl$_3$; internal standard CFCl$_3$ δppm): −81.5 (t, 3F, J=9.3 Hz, CF$_3$), −114.4 (m, 2F, CF$_2$), −124.6 (m, 2F, CF$_2$), −126.5 (m, 2F, CF$_2$).

The polymers were synthesized as follows:

Preparative Example 1

9FSEA Homopolymer

Into a 200 mL four-necked flask, the monomer (9FSEA monomer) (10 g (0.029 mol)) prepared in Synthetic Example 1 and butyl acetate (27 g) were charged and nitrogen was flowed for 60 minutes. The temperature of a flask content was increased to 60° C., Perbutyl PV (0.11 g (0.0006 mol)) dissolved in butyl acetate (1 g) was added, and the reaction was conducted for 8 hours. The step control in the reaction was conducted on the basis of a gas chromatography, and the disappearance of monomer peaks was confirmed to determine the reaction termination. After the completion of the reaction, methanol was added to the polymerized solution, giving a white starch syrup-like precipitate. A supernatant liquid was removed off by decantation and the solvent was removed by setting the precipitate in an evaporator to distill off the solvent, whereby giving a very viscous transparent liquid substance (6.7 g) (Polymer yield 67%). The polymer was identified by elemental analysis (Table 4).

Preparative Example 2

9FESEA Homopolymer

Into a 200 mL four-necked flask, the monomer (9FESEA monomer) (10 g (0.026 mol)) prepared in Synthetic Example 2 and butyl acetate (27 g) were charged and nitrogen was flowed for 60 minutes. The temperature of a flask content was increased to 60° C., Perbutyl PV (0.11 g (0.0006 mol)) dissolved in butyl acetate (1 g) was added, and the reaction was conducted for 6 hours. The step control in the reaction was conducted on the basis of a gas chromatography, and the disappearance of monomer peaks was confirmed to determine the reaction termination. After the completion of the reaction, methanol was added to the polymerized solution, giving a white starch syrup-like precipitate. A supernatant liquid was removed off by decantation and the solvent was removed by setting the precipitate in an evaporator to distill off the solvent, whereby giving a very viscous transparent liquid substance (6.2 g) (Polymer yield 62%). The polymer was identified by elemental analysis (Table 4).

Preparative Example 3

9FESEA/StA Copolymer

Into a 200 mL four-necked flask, the monomer (9FESEA monomer) (7 g (0.02 mol)) prepared in Synthetic Example 2, stearyl acrylate (StA) (3 g (0.0093 mol)) and butyl acetate (27 g) were charged and nitrogen was flowed for 60 minutes. The temperature of a flask content was increased to 60° C., Perbutyl PV (0.11 g (0.0006 mol)) dissolved in butyl acetate (1 g) was added, and the reaction was conducted for 4 hours. The step control in the reaction was conducted on the basis of a gas chromatography, and the disappearance of monomer peaks was confirmed to determine the reaction termination. After the completion of the reaction, methanol was added to the polymerized solution, giving a white starch syrup-like precipitate. A supernatant liquid was removed off by decantation and the solvent was removed by setting the precipitate in an evaporator to distill off the solvent, whereby giving a very viscous white transparent liquid substance (9.9 g) (Polymer yield 99%). The polymer was identified by elemental analysis (Table 4).

Preparative Example 4

9FESO2EA Homopolymer

Into a 200 mL four-necked flask, the monomer (9FESO2EA) (7 g (0.017 mol)) prepared in Synthetic Example 3 and butyl acetate (21 g) were charged and nitrogen was flowed for 60 minutes. The temperature of a flask content was increased to 60° C., Perbutyl PV (0.11 g (0.0006 mol)) dissolved in butyl acetate (1 g) was added, and the reaction was conducted for 5 hours. The step control in the reaction was conducted on the basis of a gas chromatography, and the disappearance of monomer peaks was confirmed to determine the reaction termination. After the completion of the reaction, methanol was added to the polymerized solution, and a white separated precipitate was filtered under reduced pressure and dried in a vacuum desiccator to give a white powder (6.8 g) (Polymer yield 97%). The polymer was identified by elemental analysis (Table 4).

Preparative Example 5

9FESO2EA/StA Copolymer

Into a 200 mL four-necked flask, the monomer (9FESO2EA) (3 g (0.073 mol)) prepared in Synthetic Example 3, stearyl acrylate (StA) (1.26 g (0.0039 mmol) and butyl acetate (12 g) were charged and nitrogen was flowed for 60 minutes. The temperature of a flask content was increased to 60° C., Perbutyl PV (0.032 g (0.002 mol)) dissolved in butyl acetate (0.4 g) was added, and the reaction was conducted for 7 hours. The step control in the reaction was conducted on the basis of a gas chromatography, and the disappearance of monomer peaks was confirmed to determine the reaction termination. After the completion of the reaction, methanol was added to the polymerized solution, and a white separated precipitate was filtered under reduced pressure and dried in a vacuum desiccator to give a white powder (3.8 g) (Polymer yield 91%). The polymer was identified by elemental analysis (Table 4).

Comparative Preparative Example 1

9FA Homopolymer

Into a 200 mL four-necked flask, 2-(perfluorobutyl)ethyl acrylate (9F-Alc/AA) (R-1420 manufactured by Daikin Chemical Sales, Ltd.) (15 g (0.047 mol)) and tetrachlorohexafluorobutane (121 g) were charged. The solution was bubbled with nitrogen for 30 minutes and then nitrogen was replaced in gas phase for 30 minutes. The temperature of a flask content was increased to 60° C., Perbutyl PV (1.61 g (0.0092 mol)) dissolved in trichloroethane (7.86 g) was added, and the reaction was conducted for 5.5 hours. The step control in the reaction was conducted on the basis of a gas chromatography, and the disappearance of monomer peaks was confirmed to determine the reaction termination. After the completion of the reaction, methanol was added to the polymerized solution, and a white starch syrup-like precipitate was separated. A supernatant liquid was removed off by decantation and the solvent was removed by setting the precipitate in an evaporator to distill off the solvent, whereby giving a very viscous transparent liquid substance (9.36 g) (Polymer yield 82%). The polymer was identified by elemental analysis (Table 4).

Comparative Preparative Example 2

9FA/StA Copolymer

Into a 100 mL four-necked flask, 2-(perfluorobutyl)ethyl acrylate (9F-Alc/AA) (R-1420 manufactured by Daikin Chemical Sales, Ltd.) (7.00 g (0.022 mol)), stearyl acrylate (StA) (3 g (0.093 mol)) and tetrachlorohexafluorobutane (56.47 g) were charged. The solution was bubbled with nitrogen for 30 minutes and then nitrogen was replaced in gas phase for 30 minutes. The temperature of a flask content was increased to 60° C., Perbutyl PV (0.75 g (0.0043 mol)) dissolved in trichloroethane (3.67 g) was added, and the reaction was conducted for 6 hours. The step control in the reaction was conducted on the basis of a gas chromatography, and the disappearance of the 9F-Alc/AA and stearyl acrylate monomer peaks was confirmed to determine the reaction termination. After the completion of reaction, methanol was added to the polymerized solution to give a white precipitate. A supernatant liquid was removed off by decantation and the solvent was removed by setting the precipitate in an evaporator to distill off the solvent, whereby giving a very viscous white opaque liquid substance (7.06 g) (Polymer yield 70.6%). The polymer was identified by elemental analysis (Table 4).

Example 1

The polymer (1.5 g) obtained in Preparative Example 1 was dissolved in HCFC-225 (150 g). After one nylon test fabric (510 mm×205 mm) was immersed in this test solution (150 g) for about 5 minutes, and the solvent was removed by centrifugal dehydrator (500 rpm, 30 seconds). The same procedure was conducted for one PET test fabric (510 mm×205 mm), one PET/cotton mixture test fabric (510 mm×205 mm) and one cotton test fabric (510 mm×205 mm). Then each test fabric was dried at 28° C. for one night.

Then, each one fabric from the nylon test fabric, the PET test fabric, the PET/cotton mixture test fabric and the cotton test fabric was treated by a pin tenter at 150° C. for 3 minutes, and each fabric was cut into halves (255 mm×205 mm). One half was used for a shower water repellency test, and the other half was used for a water repellency test and an oil repellency test. The test results are shown in Table 5.

Example 2

The polymer obtained in Preparative Example 2 was treated as in Example 1. Then the fabrics were subjected to the shower water repellency test, the water repellency test and the oil repellency test. The test results are shown in Table 5.

Example 3

The polymer obtained in Preparative Example 3 was treated as in Example 1. Then the fabrics were subjected to the shower water repellency test, the water repellency test and the oil repellency test. The test results are shown in Table 5.

Example 4

The polymer obtained in Preparative Example 4 was treated as in Example 1 with changing the solvent to butyl acetate. Then the fabrics were subjected to the shower water repellency test, the water repellency test and the oil repellency test. The test results are shown in Table 5.

Example 5

The polymer obtained in Preparative Example 5 was treated as in Example 1. Then the fabrics were subjected to the shower water repellency test, the water repellency test and the oil repellency test. The test results are shown in Table 5.

Comparative Example 1

The polymer obtained in Comparative Preparative Example 1 was treated as in Example 1 with using the solvent of HCFC-225. Then the fabrics were subjected to the shower water repellency test, the water repellency test and the oil repellency test. The test results are shown in Table 5.

Comparative Example 2

The polymer obtained in Comparative Preparative Example 2 was treated as in Example 1 with using the solvent of HCFC-225. Then the fabrics were subjected to the shower water repellency test, the water repellency test and the oil repellency test. The test results are shown in Table 5.

TABLE 4

| | Elemental Analysis | | | | | | | | | |
|---|---|---|---|---|---|---|---|---|---|---|
| | F | | C | | H | | N | | Cl | |
| | Found (%) | Calcd. (%) | Found (%) | Calcd. (%) | Found (%) | Calcd. (%) | Found (%) | Calcd. (%) | Found (%) | Calcd. (%) |
| Preparative Example 1 | 46.85 | 48.77 | 31.02 | 30.83 | 2.31 | 2.16 | 0.00 | 0.00 | 0.00 | 0.00 |
| Preparative Example 2 | 43.68 | 45.12 | 34.77 | 34.86 | 3.18 | 3.13 | 0.00 | 0.00 | 0.00 | 0.00 |
| Preparative Example 3 | 28.65 | 31.50 | 46.98 | 47.59 | 5.71 | 6.17 | 0.00 | 0.00 | 0.00 | 0.00 |
| Preparative Example 4 | 39.92 | 41.61 | 32.20 | 32.15 | 2.77 | 2.89 | 0.00 | 0.00 | 0.00 | 0.00 |
| Preparative Example 5 | 28.35 | 29.22 | 45.92 | 45.50 | 5.52 | 5.96 | 0.00 | 0.00 | 0.00 | 0.00 |

TABLE 4-continued

| | Elemental Analysis | | | | | | | | | |
|---|---|---|---|---|---|---|---|---|---|---|
| | F | | C | | H | | N | | Cl | |
| | Found (%) | Calcd. (%) | Found (%) | Calcd. (%) | Found (%) | Calcd. (%) | Found (%) | Calcd. (%) | Found (%) | Calcd. (%) |
| Comparative Preparative Example 1 | 49.43 | 53.77 | 33.11 | 33.96 | 2.47 | 2.20 | 0.00 | 0.00 | 0.00 | 0.00 |
| Comparative Preparative Example 2 | 35.91 | 37.64 | 48.06 | 47.11 | 4.84 | 5.24 | 0.00 | 0.00 | 0.00 | 0.00 |

TABLE 5

| Test fabric | Shower water repellency | Water repellency | Oil repellency |
|---|---|---|---|
| Example 1 | | | |
| Nylon | 70 | 3 | 3 |
| PET | 80 | 3 | 3 |
| PET/Cotton | 50 | 3 | 3 |
| Cotton | 50 | 3 | 3 |
| Example 2 | | | |
| Nylon | 70 | 3 | 3 |
| PET | 80 | 3 | 3 |
| PET/Cotton | 50 | 3 | 3 |
| Cotton | 0 | 3 | 3 |
| Example 3 | | | |
| Nylon | 70 | 3 | 2 |
| PET | 80 | 4 | 3 |
| PET/Cotton | 50 | 3 | 3 |
| Cotton | 50 | 3 | 3 |
| Example 4 | | | |
| Nylon | 100 | 4 | 3 |
| PET | 100 | 4 | 3 |
| PET/Cotton | 80 | 4 | 3 |
| Cotton | 70 | 7 | 3 |
| Example 5 | | | |
| Nylon | 100 | 9 | 6 |
| PET | 80 | 5 | 6 |
| PET/Cotton | 80 | 4 | 6 |
| Cotton | 80 | 3 | 6 |
| Comparative Example 1 | | | |
| Nylon | 50 | 3 | 0 |
| PET | 70 | 3 | 3 |
| PET/Cotton | 0 | 3 | 3 |
| Cotton | 0 | Fail | 3 |
| Comparative Example 2 | | | |
| Nylon | 70 | 4 | 2 |
| PET | 50 | 4 | 3 |
| PET/Cotton | 50 | 4 | 2 |
| Cotton | 0 | 4 | 2 |

The invention claimed is:

1. A surface treatment agent comprising (1) a fluorine-containing polymer and (2) water and/or an organic solvent, characterized in that the fluorine-containing polymer comprises (A) repeating units derived from (a) a fluorine-containing compound of the formula:

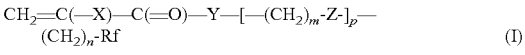

$$CH_2=C(-X)-C(=O)-Y-[-(CH_2)_m-Z-]_p-(CH_2)_n-Rf \quad (I)$$

wherein X is a hydrogen atom or a methyl group;
Y is —O— or —NH—
Z is —S— or —SO$_2$—;
Rf is a perfluoroalkyl group having 1 to 6 carbon atoms;
m is from 1 to 10, n is from 0 to 10; and
p is 0 or 1 provided that p is 1 when Y is —O—.

2. The surface treatment agent according to claim 1, which is in the form of a solution, an emulsion or an aerosol.

3. A method of treating a substrate with the surface treatment agent according to claim 1 comprising a step of immersion coating, spray coating, or foam coating, the surface treatment agent to the substrate.

4. The method according to claim 3, wherein the substrate is a textile, a masonry, a filter, a dust protective mask, a fuel cell, glass, paper, wood, leather, fur, asbestos, brick, cement, metal and oxide, ceramics, plastics, a coated surface or a plaster.

5. A textile treated with the surface treatment agent according to claim 1.

6. A carpet treated with the surface treatment agent according to claim 1.

7. A fluorine-containing compound(a') of the formula:

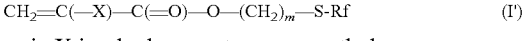

$$CH_2=C(-X)-C(=O)-O-(CH_2)_m-S-Rf \quad (I')$$

wherein X is a hydrogen atom or a methyl group;
Rf is a perfluoroalkyl group having 1 to 6 carbon atoms;
m is from 1 to 10.

8. The fluorine-containing compound according to claim 7, wherein the carbon number of the perfluoroalkyl group (Rf group) is from 1 to 4.

9. A fluorine-containing polymer comprising (A) repeating units derived from the fluorine-containing compound (a') according to claim 7.

10. The fluorine-containing polymer according to claim 9, further having:
   (B) repeating units derived from (b) a monomer free from a fluorine atom, and
   (C) optionally, repeating units derived from (c) a crosslinkable monomer,
   in addition to the repeating units (A).

11. The fluorine-containing polymer according to claim 10, wherein the fluorine atom-free monomer (b) forming the repeating units (B) is an acrylate of the general formula:

$$CH_2=CA^1COOA^2$$

wherein $A^1$ is a hydrogen atom or a methyl group, and $A^2$ is a hydrocarbon group having 1 to 30 carbon atoms.

12. The fluorine-containing polymer according to claim 10, wherein the crosslinkable monomer (c) forming the repeating units (C) is a fluorine-free monomer having at least two reactive groups and/or carbon-carbon double bonds.

13. The fluorine-containing polymer according to claim 10, wherein the amount of the fluorine atom-free monomer (b) is 0.1 to 50 parts by weight, and the amount of the crosslinkable monomer (c) is at most 20 parts by weight, based on 100 parts by weight of the fluorine-containing compound (a').

14. The surface treatment agent according to claim 1, wherein the carbon number of the perfluoroalkyl group (Rf group) is from 1 to 4.

15. The surface treatment agent according to claim 1, further having:

(B) repeating units derived from (b) a monomer free from a fluorine atom, and (C) optionally, repeating units derived from (c) a crosslinkable monomer, in addition to the repeating units (A) derived from the fluorine-containing compound (a).

16. The surface treatment agent according to claim 15, wherein the fluorine atom-free monomer (b) forming the repeating units (B) is an acrylate of the general formula:

$$CH_2=CA^1COOA^2$$

wherein $A^1$ is a hydrogen atom or a methyl group, and $A^2$ is a hydrocarbon group having 1 to 30 carbon atoms.

17. The surface treatment agent according to claim 15, wherein the crosslinkable monomer (c) forming the repeating units (C) is a fluorine-free monomer having at least two reactive groups and/or carbon-carbon double bonds.

18. The fluorine-containing polymer according to claim 15, wherein the amount of the fluorine atom-free monomer (b) is 0.1 to 50 parts by weight, and the amount of the crosslinkable monomer (c) is at most 20 parts by weight, based on 100 parts by weight of the fluorine-containing compound (a).

19. The fluorine-containing polymer according to claim 11, wherein $A^2$ is an alkyl group represented by $C_nH_{2n+1}$, wherein n=1 to 30.

20. The surface treatment agent according to claim 16, wherein $A_2$ is an alkyl group represented by $C_nH_{2n+1}$, wherein n=1 to 30.

* * * * *

UNITED STATES PATENT AND TRADEMARK OFFICE
CERTIFICATE OF CORRECTION

PATENT NO. : 7,638,575 B2
APPLICATION NO. : 10/594011
DATED : December 29, 2009
INVENTOR(S) : Yamamoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 209 days.

Signed and Sealed this

Twenty-first Day of December, 2010

David J. Kappos
*Director of the United States Patent and Trademark Office*